United States Patent [19]

Doering et al.

[11] Patent Number: 5,102,518
[45] Date of Patent: Apr. 7, 1992

[54] ELECTROPHORESIS APPARATUS AND METHOD FOR ELECTROELUTING DESIRED MOLECULES FOR FURTHER PROCESSING

[75] Inventors: Don S. Doering, Somerville; Paul T. Matsudaira, Boston, both of Mass.

[73] Assignee: Whitehead Institute for Biomedical Research, Cambridge, Mass.

[21] Appl. No.: 590,047

[22] Filed: Sep. 27, 1990

Related U.S. Application Data

[63] Continuation of Ser. No. 303,581, Jan. 27, 1989, abandoned.

[51] Int. Cl.$^5$ .............................................. G01N 27/26
[52] U.S. Cl. ............................. 204/180.1; 204/182.3; 204/182.8; 204/299 R; 204/301
[58] Field of Search ............... 204/180.1, 182.3, 182.8, 204/299 R, 301

[56] References Cited

U.S. PATENT DOCUMENTS

| | | |
|---|---|---|
| 3,129,158 | 4/1964 | Raymond et al. |
| 3,375,187 | 3/1968 | Buchler |
| 3,413,208 | 11/1968 | Barg et al. |
| 3,539,493 | 11/1970 | Dorman |
| 3,579,433 | 5/1971 | Dahlgren |
| 3,640,813 | 2/1972 | Nerenberg |
| 3,668,107 | 6/1972 | Lappe |
| 3,720,593 | 3/1973 | Juhos |
| 3,791,950 | 2/1974 | Allington |
| 3,795,600 | 3/1974 | Allington |
| 3,844,925 | 10/1974 | Stathakos |
| 3,847,785 | 11/1974 | Allington |
| 3,855,111 | 12/1974 | Allington |
| 3,914,168 | 10/1975 | Allington |
| 4,111,785 | 9/1978 | Roskam |
| 4,159,933 | 7/1979 | Allington et al. |
| 4,164,464 | 8/1979 | Allington et al. |
| 4,552,640 | 11/1985 | Kartenbeck .................. 204/301 |
| 4,632,761 | 12/1986 | Bowers et al. ................ 210/650 |
| 4,755,301 | 7/1988 | Bowers et al. ................ 210/650 |

OTHER PUBLICATIONS

S. Ihara et al., "Recovery of Polypeptides from Polyacrylamide Gels by Electrophoretic Elution in a Centrifugation Concentrator", *Analytical Biochemistry* 166, 349–352 (1987).

F. Hanaoka et al., "Recovery of Functional Proteins from Sodium Dodecyl Sulfate-Polyacrylamide Gels," *Analytical Biochemistry* 99, 170–174 (1979).

B. R. Ziola and D. G. Scraba, "Recovery of SDS--Proteins from Polyacrylamide Gels by Electrophoresis into Hydroxylapatite," *Analytical Biochemistry* 72, 366–371 (1976).

E. J. Stellwag and A. E. Dahlberg, "Electrophoretic transfer of DNA, RNA and Protein onto diabenzyloxymethyl(DBM)-paper", *Nucleic Acids Research* 8, No. 2, 299–317 (1980).

M. Otto and M. Snejdarkova, "A Simple and Rapid Method for the Quantitative Isolation of Proteins from Polyacrylamide Gels", *Analytical Biochemistry* 111, 111–114 (1981).

R. E. Stephens, "High Resolution Preparative SDS–Polyacrylamide Gel Electrophoresis: Fluorescent Visualization and Electrophoretic Elution-Concentration of Protein Bonds", *Analytical Biochemistry* 65, 369–379 (1975).

P. Karsnas and P. Roos, "Two Methods for Electrophoretic Elution of Proteins from Polyacrylamide Gels", *Analytical Biochemistry* 77, 168–175 (1977).

(List continued on next page.)

Primary Examiner—John Niebling
Assistant Examiner—David G. Ryser
Attorney, Agent, or Firm—Hamilton, Brook, Smith & Reynolds

[57] ABSTRACT

An electroelutor provides electroelution and concentration of small amounts of proteins from sample gels. The electroelutor elutes desired molecules from gels in a sample holder directly onto a membrane of a centrifuge concentrator or a sequencing membrane. After electroelution, the eluted molecules can be concentrated or processed in a sequencing device with minimized sample handling and minimized disturbance about the membrane.

12 Claims, 3 Drawing Sheets

OTHER PUBLICATIONS

R. C. Montelaro, "Protein antigen purification by preparative protein blotting", *VCH Verlagsgesellschaft, Elpho* 9/87–*Filmbelichtung-Spalte* 18–21 *Artikel* 301.

B. S. Parekh et al., "Preparative Elution of Proteins from Nitrocellulose Membranes after Separation by Sodium Dodecyl Sulfate-Polyacrylamide Gel Electrophoresis", *Analytical Biochemistry* 148, 87–92 (1985).

M. W. Hunkapiller et al., "Isolation of Microgram Quantities of Proteins from Polyacrylamide Gels for Amino Acid Sequence Analysis", *Methods in Enzymology* 91, 227–236 (1983).

M. A. Lischwe and D. Ochs, "A New Method for Partial Peptide Mapping Using N-Chlorosuccinimide/Urea and Peptide Silver Straining in Sodium Dodecyl Sulfate-Polyacrylamide Gels", *Analytical Biochemistry* 127, 453–457 (1982).

Anyaibe, et al., "Electromicroelution Chamber for Isolation of Electrophoretically Separated Proteins:", *Medical Res. Eng.*, 12(4): 16–18 (1977).

Allington, et al., "Electrophoretic Concentration of Macromolecules", *Anal. Biochem.*, Bolume 85, pp. 188–196 (1977).

ELECTROPHORESIS APPARATUS AND METHOD FOR ELECTROELUTING DESIRED MOLECULES FOR FURTHER PROCESSING

FUNDING

Work described herein relating to the present invention has been funded under contract no. DK35 306 awarded by the National Institutes of Health.

This is a continuation of co-pending application Ser. No. 07/303,581, filed on Jan. 27, 1989, now abandoned.

BACKGROUND OF THE INVENTION

Electrophoresis is the term used to describe the transport of charged particles, such as biological polymers, through a solvent by an electric field. Proteins and other charged particles can be characterized by their relative rate of movement in an electric field. Sodium dodecyl sulfate-polyacrylamide gel electrophoresis (SDS-PAGE) is a widely utilized preparative and analytical technique for the separation of proteins and peptides.

SDS-PAGE separates the proteins of interest from other proteins based upon an intrinsic charge-to-mass ratio and apparent molecular weight in the presence of SDS. The polyacrylamide gel acts as a molecular sieve through which proteins move according to size. The lower molecular weight proteins have a higher mobility. The proteins are treated with SDS and mercaptoethanol and behave as though they have a uniform shape and identical charge to mass ratio as they move through the gel by the force of the electric field. A molecular weight determination of the proteins can be made based on the migration of the protein through the gel relative to proteins of known molecular weight.

After protein separation by SDS-PAGE. it is often desirable to identify and recover an individual protein or proteins of interest from a complex mixture that has been resolved for further analysis or sequencing. Most commonly, techniques which rely on diffusion or elution are performed to remove proteins from the polyacrylamide gel. Electroelution is a technique whereby proteins are electrophoretically removed from the polyacrylamide gel for further processing or sequencing. In electroelution, the gel slab is soaked in a dye, such as Coomassie Brilliant Blue, which stains the protein previously separated by SDS-PAGE. The gel band containing the protein of interest is then excised and placed in an elution apparatus which applies an electric current that electrophoretically removes and isolates the proteins for further analysis.

A typical electroelution method is described by Hunkapiller et al., *Methods in Enzym.*, 91: 227–236 (1983). Briefly, proteins are stained by Coomassie Brilliant Blue, excised, homogenized, and placed in an elution cell capped at both ends with dialysis membrane. The elution cell bridges two electrode chambers of an electrophoresis tank and a two-channel peristaltic pump recirculates the buffer solution held in the chambers. Using an elution buffer (e.g.. 0.1% SDS in 0.05 M $NH_4HCO_3$), a constant voltage of 50V is applied for 12–16 hours which causes the negatively charged proteins to migrate from the gel toward the positive electrode. A second elution is run with a dialysis buffer (e.g., 0.02% SDS in 0.01 M $NH_4HCO_3$) at 80 volts for 20–24 hours to remove the salt and SDS. Finally, the protein is precipitated to remove any remaining detergent or salt. The protein can then be analyzed by a number of techniques for sequence determination.

Another method of electroelution is described by Anderson et al., *J. Virol.*, 12: 241 (1973), in which electroelution proceeds from a gel slice in a Pasteur pipet into a dialysis bag at the lower end of the pipet. In this method, protein can be lost due to adsorption onto the large surface area of the dialysis membrane, solutions transfers or through prolonged dialysis necessary to remove the SDS. Thus, this method is only efficient with large amounts of protein.

Although current electroelution methods provide effective recovery of proteins, the procedures are time consuming (generally one day) and the apparatus are only able to elute a limited number of samples simultaneously. Furthermore, the transfer of protein samples from the elution dialysis membrane to a concentrator or dialyzer in both of the above-described methods involves the risk of loss of sample proteins or polypeptides thereof.

An electroelutor device which elutes protein from gel pieces directly into a concentrator sample reservoir is described by S. Ihara et al. in "Recovery of Polypeptides from Polyacrylamide Gels by Electrophoretic Elution in a Centrifugation Concentrator", *Analytical Biochemistry*, 166 pg. 349–352 (1987). A commercially available concentrator is made to hold a sample tube of gel slices at an upper end and is then placed inverted (upside down) in a bath of elution buffer. Desired protein is eluted from the sample tube in an upward direction against gravity toward the membrane of the concentrator. After electrophoretic elution the concentrator and unit containing the bath of elution buffer is inverted. The concentrator now being reoriented to a right side up position is ready for centrifugal concentration or salt exchange without transfer of the eluted protein.

Although this method maximizes sample recovery by minimizing sample handling, the upside down orientation of the concentrator poses various disadvantages and difficulties. For example, the sample tube holding subject gel slices must be secured to the end of the concentrator and closed off by a dialysis membrane in order to allow the concentrator to be held upside down in the bath of elution buffer during elution. Also, the elution against gravity requires immediate inversion of the apparatus once supply of the electric field to the elution buffer is ceased. Otherwise eluted molecules fall back into the sample tube under the force of gravity, and the amount of actual sample recovery is decreased.

Accordingly, there is a need for an electroelution device which simplifies operation and minimizes sample loss.

SUMMARY OF THE INVENTION

The foregoing problems of the prior art are overcome by the electrophoresis apparatus and method of the present invention. An electrophoresis apparatus based on the principles of the present invention employs a tube assembly, an upper buffer chamber and a lower buffer chamber The upper buffer chamber is stacked on top of the lower buffer chamber, and each chamber holds an amount of elution liquid to which an appropriate electric field is applied.

The tube assembly comprises a main tube with an upper portion immersed in the elution liquid of the upper buffer chamber and a lower portion immersed in the elution liquid of the lower buffer chamber. The main tube also holds an amount of elution liquid. Removably retained in an upper portion of the main tube is a sample holder which holds sample gel pieces and elution liquid. The elution liquid in the sample holder is in fluid communication with the elution liquid in the upper buffer chamber and the main tube. Positioned in the lower portion of the main tube is a membrane for collecting eluted molecules.

An electrical current is passed through the elution liquid in the upper and lower buffer chambers and causes desired molecules (e.g. protein, DNA) in the sample gel pieces to be eluted out of the gel pieces, through a lower end of the sample holder, through the main tube and onto the membrane in the lower portion of the main tube. The membrane retains the eluted molecules in a manner suitable for direct further processing. In addition, the orientation of the main tube enables subsequent processing without further preparation or reorientation of the main tube and hence, without disturbing the eluted molecules retained on the membrane.

In accordance with one aspect of the present invention the main tube is preferably a concentrator of a centrifugal filtration system. After elution, the concentrator tube may be removed from the electrophoresis apparatus and directly centrifuged to concentrate the eluted molecules by filtration. The minimized handling of the molecules and the concentrator optimizes recovery of desired molecules.

In another embodiment of the present invention, the main tube has a lower portion which is cone shaped narrowing toward a membrane. Such a shape directs eluted molecules toward the membrane for collection thereon during electrophoresis. In addition, the membrane may be a sequencing membrane and is removable from the cone shaped end of the main tube so that direct use of the membrane in a sequencing process may follow elution. With the sequencing membrane being the membrane onto which the desired molecules are eluted, there is minimal sample loss.

In another aspect of the present invention, bubble removing means are employed. During positioning of the tube assembly in the lower and upper buffer chambers, gas bubbles form beneath the main tube in the lower buffer chamber. These bubbles block electric current such that elution is not achieved. A Pasteur pipet with a bent end may be used to withdraw the bubbles from under the main tube. After removal of the bubbles by this or other suitable processes, the electrical current is passed through the elution buffer to provide the desired electrophoretic elution.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

The present invention provides an electrophoresis apparatus and method which elutes desired molecules from subject gels onto a membrane designed for further processing of the molecules. The eluted molecules are retained on the membrane in a configuration which is directly ready for further processing without transfer of the eluted molecules and with minimum handling or disturbance of the membrane to prevent loss of the recovered molecules.

Figures 3, 4:
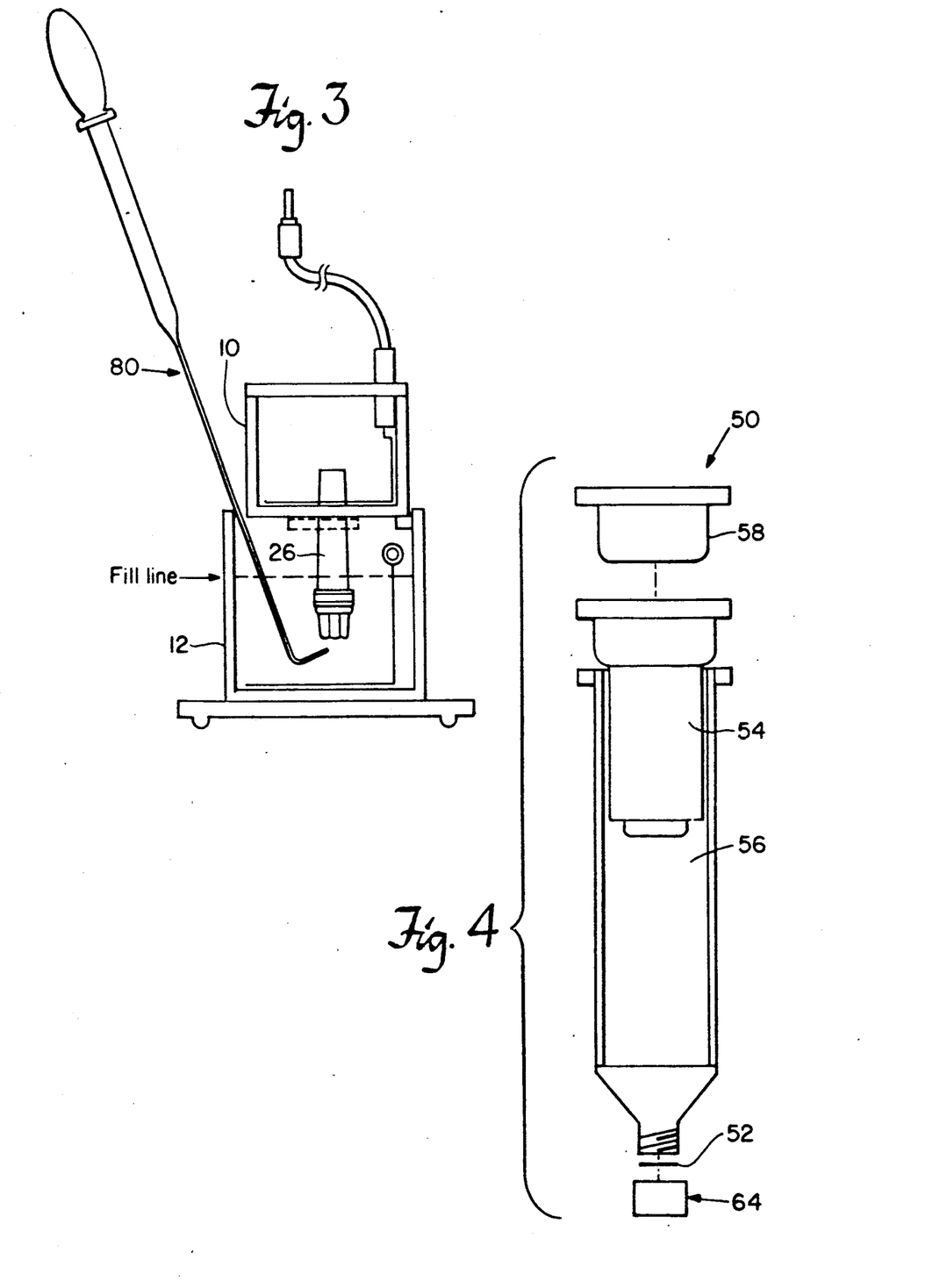
FIG. 3 is a schematic illustration of use of a bent pipet to remove bubbles from beneath a tube assembly in the apparatus of FIG. 1.
FIG. 4 is a partially exploded view of another tube assembly of the present invention.

In a primary example of the present invention, microgram quantities (1 to 100 $\mu$g) of protein or DNA are electrophoretically eluted from sample gel pieces 30 onto a low-adsorptive membrane 38 in a centrifugal concentrator 26 shown in FIG. 1 or onto a sequencing membrane 52 usable in an automated protein sequencer as shown in FIG. 4 and described in detail later. The electroelutor apparatus 48 of FIG. 1 applies an electric field between the tops and bottoms of the gel pieces 30 and moves the protein or DNA through the gel pieces and onto the target membrane 38 with the centrifugal concentrator 26 in a upright position. After elution, the centrifugal concentrator 26, holding the recovered molecules on its membrane 38 and the amount of elution buffer contained therein, may be removed from the electroelutor apparatus and placed in a centrifuge for centrifugal concentration or buffer exchange without further handling of the recovered molecules or further preparation/reorientation of the centrifugal concentrator 26. Since the concentrator 26 is in an upright position, the recovered molecules are held substantially undisturbed in the concentrator 26 during the transfer from the electroelution apparatus 48 to the centrifuge. Centrifugal concentration and/or buffer exchange is then performed by procedures common in the art; such as those disclosed by U.S. Pat. No. 4.632,761 and U.S. Pat. No. 4,755,301, the contents of which are herein incorporated by reference.

Figure 1:
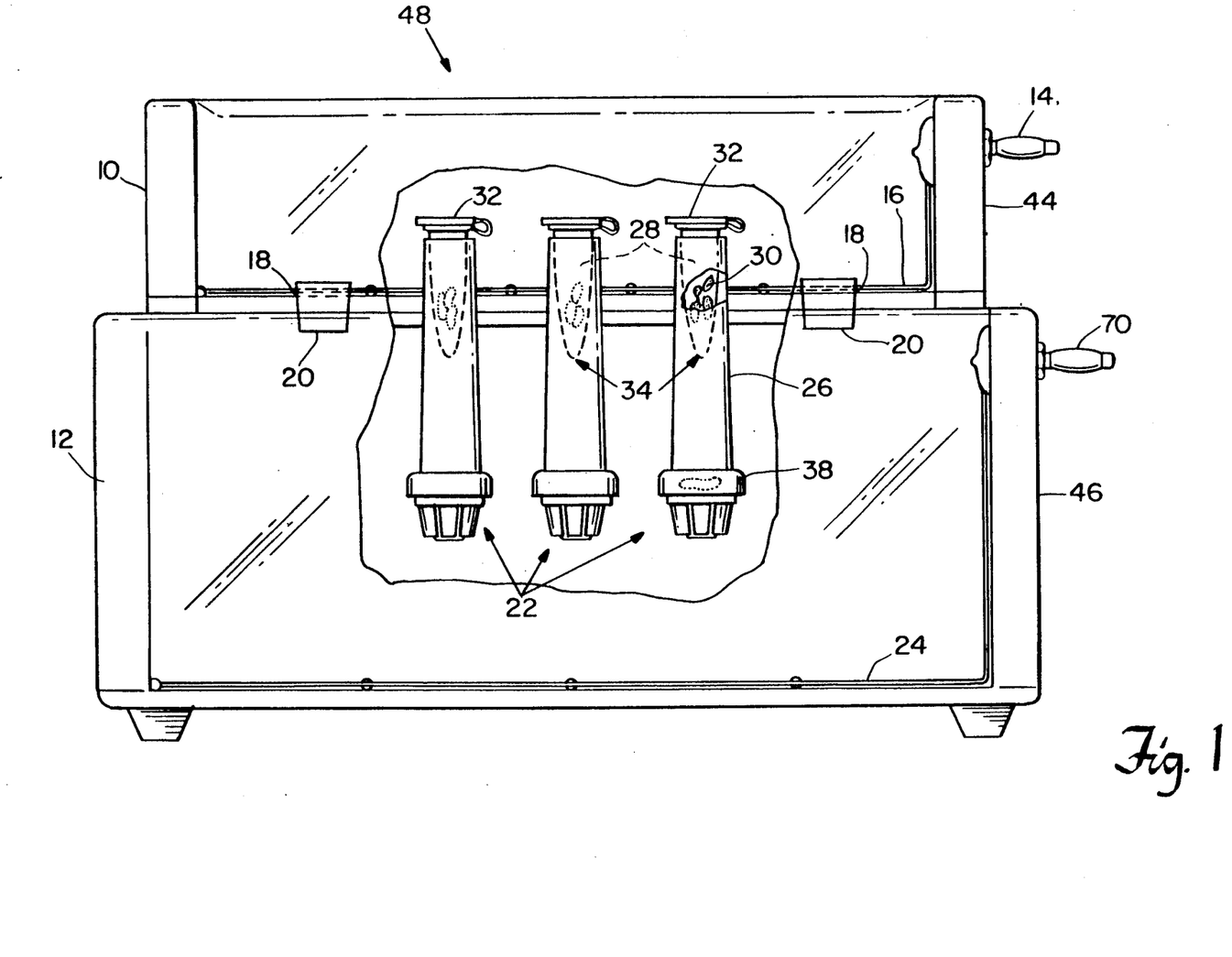
FIG. 1 is a schematic view partially cut away of an electrophoresis apparatus embodying the present invention.

Referring now to FIG. 1 in detail, the electroelution apparatus 48 embodying the present invention includes an upper open box-like chamber 10 and a lower open box-like chamber 12. Upper chamber 10 sits on a ledge or a similar wall element attached to and positioned about the inner circumference of the open surface of chamber 12. Each chamber 10, 12 holds an amount of elution buffer or fluid sufficient to immerse opposite ends of concentrator 26 when the apparatus is fully assembled. The elution buffer in each chamber becomes electrically charged by respective current carrying wires 16 and 24. Wire 16 runs along the length of one side of the inside bottom surface of upper chamber 10 and is connected to a negative electrical terminal 14 which protrudes through an end wall 44 of chamber 10. In a similar manner. wire 24 runs along the length of one side of the inside bottom surface of lower chamber 12 and is connected to positive electrical terminal 70 which protrudes through an end wall 46 of lower chamber 12. Preferably, wires 16 and 24 comprise platinum, but other wires of other conducting materials are suitable.

Power is supplied to wires 16 and 24 from a constant voltage power supply as is common in the art through lead wires 40, 42 (shown in FIG. 2) which are connected or connectable to terminals 14 and 70. The power is supplied, for example, at a level of about 100-400 volt-hours In a preferred embodiment, the connection between terminals 14, 70 and the lead wires 40, 42 is made through a safety cover 36 illustrated in FIG. 2. Safety cover 36 is shaped to cover upper chamber 10 and any exposed entrance into lower chamber 12 through the open surface of chamber 12. An elongated side of cover 36 lies spaced apart from end walls 44, 46 of chambers 10, 12 respectively and carries two connectors 60, 62 for removably receiving electrical terminals 14 and 70 respectively. An electrical connection between terminals 14, 70 and connectors 60, 62 cannot be made unless safety cover 36 is properly positioned on chambers 10, 12. In that case, an electrical connection cannot be made unless safety cover 36 is blocking access into chambers 10 and 12 through their respective open surfaces. Hence, electrocution of objects not intended to be in either chamber is prevented or at least minimized.

In the bottom wall of upper chamber 10 there are a number of apertures 18, such as five shown in FIG. 1. The apertures 18 are of a shape and size which receive and removeably retain plugs 20 or tube assemblies 22 (FIG. 1) and 50 (FIG. 4) described later. The plug holding apertures 18 provide ports for draining elution buffer from chamber 10 where plugs 20 close those apertures during electroelution processing.

Tube assemblies 22 are positioned in respective apertures 18 of the upper chamber 10 in a manner which immerses an upper portion of the tube assembly in the elution buffer of the upper chamber 10 and immerses a lower portion of the tube assembly in the elution buffer of the lower chamber 12. The main member of a tube assembly 22 is a centrifugal concentrator 26, preferably of the type with a low adsorptive membrane 38 (i.e. a membrane designed for low retention of proteins and for filtration) and designed for the concentration or desalting of proteins. Such a concentrator 26 as shown in FIG. 1 is a Centricon device manufactured by Amicon., division of W.R. Grace and Co., Connecticut and described in U.S. Pat. No. 4,632,761. The tapered outer shape of the concentrator 26 prevents leakage of elution buffer from upper chamber 10 into lower chamber 12 when concentrator 26 is positioned in an aperture 18.

In the upper end of centrifugal concentrator 26, a sample holder 28 is snugly accommodated and removably retained. The sample holder 28 is a standard laboratory 500 μg tube or the like with a snap on cap 32 for containing subject gel pieces 30. The cap 32 prevents gel pieces 30 from floating out of sample holder 28 when immersed in the elution buffer of chamber 10. The cap 32 and conical tip end 34 of sample holder 28 have pin holes therethrough which allow passage of electric current and which enable elution buffer to flow through sample holder 28 in fluid communication with elution buffer in upper chamber 10 and elution buffer in concentrator 26. Also, the pinholes are of a small enough diameter to prevent gel pieces 30 from falling into tube 26. The pin hole in the conical end 34 further allows passage of eluted molecules from the sample holder 28 into the interior of concentrator 26.

Specifically, the force of the applied electric field during elution draws the negatively charged eluted molecules from the gel pieces 30 in sample holder 28 toward the positively charged wire 24 in lower chamber 12 in a direction with gravity. Membrane 38 being situated between sample holder 28 and wire 24 intercepts and retains the travelling eluted molecules. Little to no gravitational effects exist since the electric field force is greater than the gravitational field force. Further, no gravitational force opposes the electrical force since the forces are in the same direction. After elution, when application of the electric field is ceased, the eluted molecules are no longer under the forces of the electric field and tend to hover on or near the membrane 38 under gravitational forces. With the concentrator 26 in an upright position, retention of the eluted molecules on the small surface area of the membrane 38 is maximized both during electroelution and just after electrophoresis, under influence of the foregoing forces (i.e. electric field and gravity).

Use of the electroelution apparatus 48 is then as follows Protein or other desired molecule containing gel slices are placed into a sample holder 28. Maceration of gel slices is not necessary, but may aid in the rapid and efficient elution of some samples. A centrifugal concentrator 26 is firmly inserted into the apertures 18 in the upper chamber 10 through the outside bottom surface of the chamber. The lower chamber 12 is filled with elution buffer so that the buffer level is above the membrane 38 of the concentrator 26 when the elutor apparatus 48 is fully assembled.

The upper chamber 10 is placed to sit on the ledge at the upper edge of the lower chamber 12. Air bubbles that have been trapped beneath the concentrators 26 are dislodged and removed with a bent Pasteur pipet 80 as shown in FIG. 3. After the bubbles are removed the pipet 80 is removed from the lower chamber 12.

The upper chamber 10 and the concentrators 26 are filled with elution buffer so that the buffer completely covers the concentrators. The conical tip end 34 of sample holder 28 is perforated with a syringe needle or other sharp pin-like device to allow elution of the protein. Likewise the cap 32 of sample holder 28 is perforated to allow the holder to fill with elution buffer when placed in the top end of concentrator 26. Sample holder 28 is inserted into the top end of concentrator 26 so that it fits securely in the interior concentrator 26.

Figure 2:
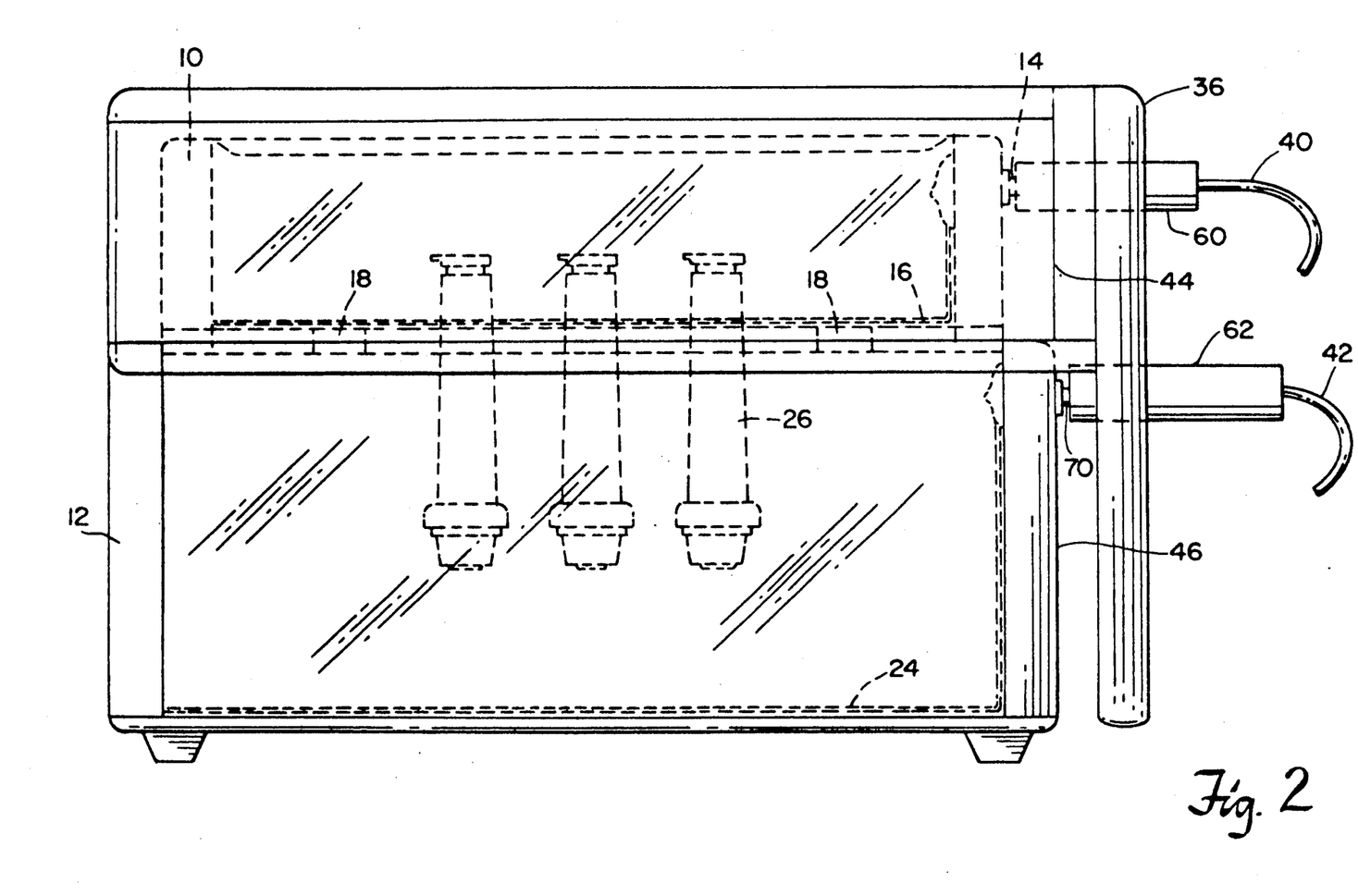
FIG. 2 is a schematic view of the electrophoresis apparatus of FIG. 1 with a safety cover thereon.

Thereafter, the safety cover 36 is slid onto the upper chamber 10 until proper connections with the connectors 60, 62 in the cover and the terminals 14, 70 on the upper and lower chambers 10, 12 are made. The wires or leads 40, 42 from the connectors 60, 62 of safety cover 36 are plugged into a standard laboratory constant voltage power supply. The power is turned on and electrophoresis is allowed to proceed for a desired length of time.

After electroelution is completed, the safety cover 36 is removed, and the upper buffer chamber 10 is drained with the removal of plugs 20 from drain ports 18. The sample holder 28 is then lifted from the concentrator 26 and the elution buffer in the holder is allowed to drain into the concentrator 26. The concentrator may now be removed from upper chamber 10, and the electroeluted protein or molecules may be concentrated and the buffer exchanged according to standard procedure (i.e with a centrifuge, etc.).

A second type of tube assembly 50 useable in the electroelution apparatus 48 is illustrated in FIG. 4. This tube assembly has approximately the same length and outer diameter as centrifugal concentrator 26 but contains a small removable sequencing membrane 52 near the base of its conical tip. This membrane is preferably a PVDF membrane such as the one called Immobilon manufactured by Millipore Corp.

Tube assembly 50 has a sample container 54 for holding subject gel pieces 30. Sample container 54 has a perforated top and a plastic mesh bottom. The top 58 fits into the upper end of sample container 54 and prevents subject gel pieces from floating out when the tube assembly 50 is immersed in the elution buffer of upper chamber 10. The perforated top and mesh bottom allow the passage of elution buffer, electrical current and eluted molecules through container 54.

The sample container 54 fits snugly into the top end of main elution tube 56. Main tube 56 is shaped and sized to fit into aperture 18 (FIG. 1) of upper chamber 10. The lower end of the main elution tube 56 is cone shaped pointing downward. At the narrow end of the conical end, the sequencing membrane 52 is held securely in place by an o-ring cap 64. The o-ring cap 64 screws tightly onto the cone end to seal the membrane 52 onto the bottom end of the main tube 56 and screws off for easy removal of the membrane after electrophoresis. Further the cone shape provides direction for and concentration of eluted molecules onto the small surface area of membrane 52.

Use of tube assembly 50 is then as described above for tube assemblies 22. The applied electric current is passed through the sample container 54 and main tube 56, and protein or other molecules in the gel pieces 30 are electrophoresed through the mesh end of the sample container 54 and onto the sequencing membrane 52. The eluted molecules are closely collected on the membrane 52 due to the cone shaped end of main tube 56.

After elution the tube assembly 50 is removed from the apparatus in a manner similar to that described for tube assemblies 22. The o ring cap 64 is unscrewed and removed to provide easy access to membrane 52 with eluted molecules held thereon. The sequencing membrane 52 is removed from main tube 56 and placed directly on the sample holder of a gas phase protein sequencer or the like. To that end, protein bands from the sample gel slices are sequenced directly from the membrane 52.

The foregoing sequencing is made possible by the tube assembly 50 concentrating the protein from a large number of gel pieces onto a small area of a sequencing membrane 52. In the preferred embodiment, the electroelution apparatus 48 permits the sequencing of proteins available only in small quantities (10 to 100 picomoles) at low concentrations (0.001-0.1 μg per mm). The high yield electrophoretic concentration of the protein reduces the need for less efficient concentration and purification steps of these rare proteins.

The following non-limiting example further illustrates the present invention.

EXAMPLE

Method

Bovine Serum Albumin (BSA) was labelled with Na$^{125}$I using the Iodobead method (Pierce Chem. Co ) to an approximate specific activity of 10 μCi/mg. Free Na$^{125}$ was removed by gel filtration, followed by exhaustive dialysis. $^{125}$I-BSA was electrophoresed on 10% SDS gels according to standard methods. Radioactive gel slices were cut out of unfixed gels, placed in the micro-electroelutor gel holders, and counted to obtain "initial" counts. Electroelution was performed in standard SDS-PAGE gel running buffer (Tris-Glycine-SDS) diluted 1:1 v/v with water for approximately 400 Volt-hours. After electroelution, gel slices were counted to obtain "remaining" counts. Eluted counts were concentrated in the Centricon concentrator and counted to obtain "eluted" counts.

Results

The recovery $^{125}$I-BSA from unfixed SDS-PAGE gels was generally 90-95%.

Approximately 2.5% of initial counts remained in the gel slice.

Approximately 2.5% of initial counts remained bound to the Centricon membrane.

While the invention has been particularly shown and described with reference to a preferred embodiment thereof, it will be understood by those skilled in the art that various changes in form and details may be made therein without departing from the spirit and scope of the invention as defined by the appended claims.

We claim:

1. A method of eluting desired molecules from sample gel pieces onto a target membrane usable for further processing comprising the steps of:
(a) providing electrophoresis apparatus having:
   an upper buffer chamber holding elution liquid;
   a lower buffer chamber holding elution liquid and positioned vertically adjacent the upper buffer chamber;
   a tube assembly having (i) a main tube with an upper portion immersed in the elution liquid in the upper buffer chamber and a lower portion immersed in the elution liquid of the lower buffer chamber, and the main tube holding an amount of elution liquid, (ii) a sample holder removeably retained in the upper portion of the main tube and holding sample gel pieces and elution liquid, the elution liquid in the sample holder being in fluid communication with elution liquid in the upper buffer chamber and elution liquid in the main tube, and (iii) a membrane positioned in the lower portion of the main tube for retaining eluted molecules; and
   electrical means for passing an electrical current through the elution liquid in the upper and lower buffer chambers such that desired molecules are eluted from the sample gel pieces in a direction with gravity and are retained on the membrane on the lower portion of the main tube;
(b) removing any bubbles beneath the tube assembly; and
(c) maximizing recovery of desired molecules by
   (1) passing an electrical current through the elution liquid in the electrophoresis apparatus to elute desired molecules from sample gel pieces onto the membrane with the membrane in an orientation ready for further processing, the membrane maximizing retention of the desired molecules relatively undisturbed until further processing begins; and
   (2) removing at least the main tube from the upper and lower buffer chambers maintaining the membrane in the orientation ready for further processing, such that the desired molecules remain relatively undisturbed on the membrane during removal of the main tube from said chambers.

2. A method as claimed in claim 1 wherein the main tube is a concentrator tube for centrifugally concentrating the desired molecules retained on the membrane; and the method further comprises the step of centrifuging the main tube to concentrate the desired molecules.

3. A method as claim 1 wherein the membrane is a sequencing membrane and is removable from the main tube; and the method further comprises the steps of:
removing the membrane from the main tube; and
processing the membrane is a sequencing device such that sequence processing is obtained directly after elution.

4. Electrophoresis apparatus for eluting desired molecules from sample gel pieces comprising:
an upper buffer chamber holding elution liquid;
a lower buffer chamber holding elution liquid and positioned vertically adjacent the upper buffer chamber along a longitudinal axis;
a tube assembly:
(i) a concentrator tube for centrifugally concentrating desired molecules after elution, the concentrator tube having an upper portion immersed in the elution liquid of the upper buffer chamber and a lower portion immersed in the elution liquid of the lower buffer chamber, and the concentrator tube holding an amount of elution liquid, and
(ii) a sample holder removably retained in the upper portion of the concentrator tube and holding sample gel pieces and elution liquid, the elution liquid in the sample holder being in fluid communication with elution liquid in the upper buffer chamber and elution liquid in the concentrator tube;
electrical means for passing an electrical current through the elution fluid in the upper and lower buffer chambers such that desired molecules are eluted from the sample gel pieces in a direction with gravity and are collected in a lower portion of the concentrator tube with the concentrator tube in an orientation ready for centrifugal processing such that the desired molecules are held relatively undisturbed in the lower portion of the concentrator tube until centrifugal processing begins, the tube assembly maximizing retention of desired molecules such that the tube assembly maximizes recovery of desired molecules; and
bubble removing means for removing gas bubbles from beneath the tube assembly before the electrical current is passed through the elution liquid.

5. Apparatus as claimed in claim 1 wherein the concentrator tube comprises a low retention membrane positioned in the lower portion of the concentrator tube for retaining eluted molecules.

6. Apparatus as claimed in claim 4 wherein the bubble removing means includes a Pasteur pipet with a bent distal end.

7. Electrophoresis apparatus for eluting desired molecules from sample gel pieces comprising;
an upper buffer chamber holding elution liquid;
a lower buffer chamber holding elution liquid and positioned vertically adjacent the upper buffer chamber; a tube assembly having:
(i) a main tube with an upper portion immersed in the elution liquid of the upper buffer chamber and a lower portion immersed in the elution liquid of the upper buffer chamber and a lower portion immersed in the elution liquid of the lower buffer chamber, and the main tube holding an amount of elution liquid;
(ii) a sample holder removeably retained in the upper portion of the main tube and holding sample gel pieces and elution liquid in fluid communication with elution liquid in the upper buffer chamber and elution liquid in the main tube; and
(iii) a membrane positioned in the lower portion of the main tube for retaining eluted molecules;
electrical means for passing an electrical current through the elution liquid in the upper and lower buffer chambers such that desired molecules are eluted from the sample gel pieces in a direction with gravity and are retained on the membrane in the lower portion of the main tube in a manner which holds the desired molecules relatively undisturbed until further processing beings and in an orientation ready for said further processing, the membrane maximizing retention of desired molecules such that the tube assembly maximizes recovery of desired molecules; and bubble moving means for removing gas bubbles from beneath the tube assembly before the electrical current is passed through the elution liquid.

8. Apparatus as claimed in claim 7 wherein the main tube is a concentrator tube for centrifugally concentrating the desired molecules using centrifugal processing.

9. Apparatus as claimed in claim 7 wherein the lower portion of the main tube is conical in shape narrowing toward the membrane such that eluted molecules are directed toward the membrane for retention thereon.

10. Apparatus as claimed in claim 7 wherein the membrane is a sequencing membrane and is removable from the main tube for direct use in sequence processing.

11. In an electrophoresis apparatus, a tube assembly for eluting desired molecules from subject gel pieces, the tube assembly comprising:
a main tube having a cone shaped lower end, the cone shape narrowing downward toward a membrane held therein;
a removable cap for holding the membrane in the lower end of the main tube; a sample container removeably retained in an upper end of the main tube, the sample container for holding gel pieces containing desired molecules to be eluted, the sample container vented at opposite ends to allow passage of electric current, elution buffer and eluted molecules, during application of an electric field the eluted molecules passing from the sample container through the main tube to the membrane for retention thereon, the cone shape of the lower end of the main tube concentrating eluted molecules on the membrane, the eluted molecules being held relatively undisturbed on the membrane until subsequent processing begins.

12. A tube assembly as claimed in claim 11 wherein:
the membrane is a sequencing membrane; and
the removably cap provides access to the membrane after electroelution in a manner which enables direct use of the membrane with eluted molecules retained thereon in a sequencing process.

* * * * *

UNITED STATES PATENT AND TRADEMARK OFFICE
CERTIFICATE OF CORRECTION

PATENT NO. : 5,102,518

DATED : April 7, 1992

INVENTOR(S) : Don S. Doering and Paul T. Matsudaira

It is certified that error appears in the above-identified patent and that said Letters Patent is hereby corrected as shown below:

In Claim 5, line 1 of that claim, delete "Claim 1" and insert ---Claim 4---.

In column 10, line 23 delete "moving" and insert ---removing---.

In Claim 11, line 8 of that claim, after "tube;" insert a new paragraph.

Signed and Sealed this

Twentieth Day of July, 1993

Attest:

MICHAEL K. KIRK

Attesting Officer     Acting Commissioner of Patents and Trademarks